US010239085B2

(12) United States Patent
Paunescu et al.

(10) Patent No.: US 10,239,085 B2
(45) Date of Patent: Mar. 26, 2019

(54) ASEPTIC AEROSOL MISTING DEVICE

(71) Applicant: Johnson & Johnson Consumer Inc., Skillman, NJ (US)

(72) Inventors: Alexandru Paunescu, Skillman, NJ (US); John Rytel, Skillman, NJ (US); James C. Menke, Califon, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/337,064

(22) Filed: Oct. 28, 2016

(65) Prior Publication Data

US 2017/0128971 A1    May 11, 2017

Related U.S. Application Data

(60) Provisional application No. 62/248,682, filed on Oct. 30, 2015.

(51) Int. Cl.
*A61M 11/00* (2006.01)
*B05B 17/06* (2006.01)
*A61M 15/00* (2006.01)

(52) U.S. Cl.
CPC ......... *B05B 17/063* (2013.01); *A61M 11/005* (2013.01); *A61M 15/0085* (2013.01); *B05B 17/0669* (2013.01); *A61M 2205/8206* (2013.01)

(58) Field of Classification Search
CPC ... B05B 17/06; B05B 17/063; B05B 17/0607; B05B 17/0623; B05B 17/0669;
(Continued)

(56) References Cited

U.S. PATENT DOCUMENTS

| 3,812,854 A | 5/1974 | Michaels et al. |
| 4,004,736 A | 1/1977 | George |

(Continued)

FOREIGN PATENT DOCUMENTS

| BE | 1013167 A3 | 10/2001 |
| CA | 2082499 A1 | 11/1991 |

(Continued)

OTHER PUBLICATIONS

U.S. Appl. No 15/337,325, filed Oct. 28, 2016, Johnson & Johnson Consumer Inc.

(Continued)

*Primary Examiner* — Darren W Gorman
*Assistant Examiner* — Juan C Barrera

(57) ABSTRACT

A handheld misting device has a housing having a dispensing window is arranged and configured to contain a sonic generator, a power source coupled to the sonic generator, at least one reservoir containing a liquid, and a conduit extending from the at least one reservoir to a nozzle removably coupled to the sonic generator. The sonic generator includes a converter and an elongate horn having a proximal end coupled to the converter and a distal end, and the nozzle is removably coupled to the distal end of the horn. Thus, the device delivers the liquid through a delivery opening formed in the nozzle, and activating the sonic generator energizes the liquid in the nozzle to generate an aerosol plume that is delivered through the dispensing window.

5 Claims, 4 Drawing Sheets

(58) Field of Classification Search
CPC ............ B05B 17/0646; B05B 17/0676; A61M 11/005; A61M 15/0085; A61M 2205/8206; A61M 11/007; A61M 11/042; A61M 15/0048; A61M 15/0061
USPC ...................... 239/102.2; 128/200.14–200.19
See application file for complete search history.

(56) References Cited

U.S. PATENT DOCUMENTS

| | | | |
|---|---|---|---|
| 4,085,893 A | | 4/1978 | Durley, III |
| 4,301,968 A | | 11/1981 | Berger et al. |
| 4,696,719 A | | 9/1987 | Bischoff |
| 4,877,989 A | * | 10/1989 | Drews ................. B05B 17/0623 |
| | | | 128/200.16 |
| 5,104,042 A | | 4/1992 | McKown |
| 5,166,000 A | | 11/1992 | Singh et al. |
| 5,307,640 A | | 5/1994 | Fawzy et al. |
| 5,515,842 A | * | 5/1996 | Ramseyer ......... A61M 15/0085 |
| | | | 128/200.14 |
| 5,632,445 A | | 5/1997 | Dubruque |
| 5,957,124 A | | 9/1999 | Lloyd et al. |
| 6,478,754 B1 | | 11/2002 | Babaev |
| 6,521,067 B1 | | 2/2003 | Clark |
| 6,601,581 B1 | * | 8/2003 | Babaev ............. A61M 15/0085 |
| | | | 128/200.16 |
| 6,669,103 B2 | | 12/2003 | Tsai |
| 6,837,445 B1 | | 1/2005 | Tsai |
| 6,863,224 B2 | | 3/2005 | Terada et al. |
| 6,901,926 B2 | | 6/2005 | Yamamoto et al. |
| 7,550,897 B2 | | 6/2009 | Hailes |
| 7,679,262 B2 | | 3/2010 | Meng et al. |
| 7,878,991 B2 | * | 2/2011 | Babaev .......... A61B 17/320068 |
| | | | 600/2 |
| 7,896,539 B2 | | 3/2011 | Babaev |
| 7,976,135 B2 | | 7/2011 | Brown et al. |
| 7,977,849 B2 | | 7/2011 | Hailes et al. |
| 8,016,209 B2 | | 9/2011 | Hess et al. |
| 8,061,629 B2 | * | 11/2011 | Tranchant .............. A45D 34/02 |
| | | | 239/102.2 |
| 8,123,502 B2 | | 2/2012 | Blakey et al. |
| 8,162,628 B2 | | 4/2012 | Meng et al. |
| 8,191,982 B2 | | 6/2012 | Brown et al. |
| 8,286,629 B2 | | 10/2012 | Esaki et al. |
| 8,297,947 B2 | | 10/2012 | Vanrensburg et al. |
| 8,317,299 B2 | | 11/2012 | Brown |
| 8,430,338 B2 | | 4/2013 | Duru et al. |
| 8,434,473 B2 | | 5/2013 | Tsai et al. |
| 8,720,434 B2 | * | 5/2014 | Imai .................... A61M 11/007 |
| | | | 128/200.14 |
| 8,821,802 B2 | | 9/2014 | Haran |
| 9,067,427 B2 | | 6/2015 | Hayashi |
| 9,068,566 B2 | | 6/2015 | Ivri |
| 9,168,555 B2 | | 10/2015 | Tsai et al. |
| 9,549,753 B2 | | 1/2017 | Gordon |
| 9,565,870 B2 | | 2/2017 | Deo et al. |
| 2003/0199083 A1 | * | 10/2003 | Vilendrer ............... C12M 21/08 |
| | | | 435/297.2 |
| 2003/0234298 A1 | | 12/2003 | Chen |
| 2004/0045547 A1 | | 3/2004 | Yamamoto et al. |
| 2009/0133691 A1 | * | 5/2009 | Yamada ............... A61M 11/041 |
| | | | 128/200.16 |
| 2010/0068080 A1 | | 3/2010 | Meng et al. |
| 2010/0072299 A1 | | 3/2010 | Hsieh et al. |
| 2011/0268605 A1 | | 11/2011 | Haran |
| 2011/0277491 A1 | | 11/2011 | Wu et al. |
| 2012/0279533 A1 | | 11/2012 | Kato et al. |
| 2012/0318260 A1 | | 12/2012 | Hsieh et al. |
| 2013/0108748 A1 | | 5/2013 | Deo et al. |
| 2014/0184095 A1 | | 7/2014 | Yoshinaga et al. |
| 2015/0014433 A1 | | 1/2015 | Albert et al. |
| 2015/0014434 A1 | | 1/2015 | Fedorov |

FOREIGN PATENT DOCUMENTS

| | | |
|---|---|---|
| EP | 0416106 A1 | 3/1991 |
| EP | 0615470 B1 | 12/1995 |
| EP | 2413030 A3 | 6/2013 |
| GB | 807080 | 1/1959 |
| JP | 08332425 | 12/1996 |
| JP | 09173925 | 7/1997 |
| JP | 10005711 | 1/1998 |
| WO | WO1993/10910 A1 | 6/1993 |
| WO | WO1996/09846 A1 | 4/1996 |
| WO | WO2008/097645 A1 | 8/2008 |
| WO | WO2014/165694 A2 | 10/2014 |

OTHER PUBLICATIONS

U.S. Appl. No 15/337,365, filed Oct. 28, 2016, Johnson & Johnson Consumer Inc.
U.S. Appl. No 15/337,417, filed Oct. 30, 2016, Johnson & Johnson Consumer Inc.
International Search Report, PCT Application No. PCT/US2016/059274, dated Feb. 3, 2017.
International Search Report, PCT Application No. PCT/US2016/059265, dated Feb. 3, 2017.
International Search Report, PCT Application No. PCT/US2016/059270, dated Jan. 12, 2017.
International Search Report, PCT Application No. PCT/US2016/059266, dated Feb. 3, 2017.

* cited by examiner

Fig. 3
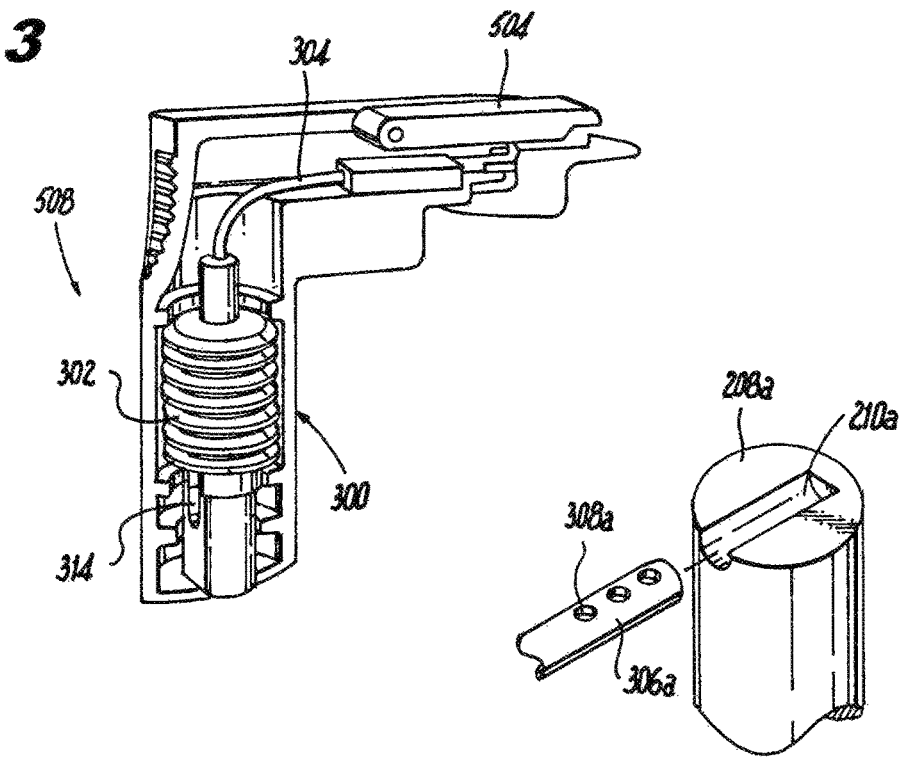
Fig. 4A
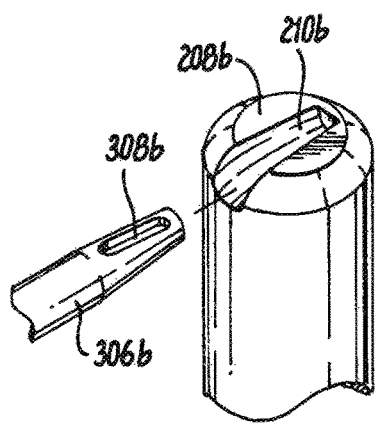
Fig. 4B
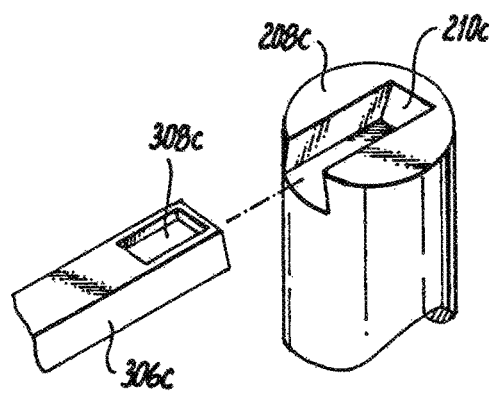
Fig. 4C

ASEPTIC AEROSOL MISTING DEVICE

CROSS-REFERENCE TO RELATED APPLICATION

This application claims the benefit of U.S. provisional application 62/248,682, filed Oct. 30, 2015, the complete disclosure of which is hereby incorporated herein by reference for all purposes.

FIELD OF THE INVENTION

The present invention relates to an aseptic misting device employing a permanent sonic generator and a replaceable liquid reservoir and nozzle.

BACKGROUND OF THE INVENTION

Spray and/or misting devices are often used to delivery cosmetic and general health care liquids. Low cost systems employ droppers and/or squeeze bottles with some form of nozzle through which the liquid is forced to provide a relatively uncontrolled dosage and droplet size.

Expensive systems may employ metering pumps and/or expensive aerosol forming components. For example, Hseih et al. U.S. Pat. No. 7,992,800 and Hseih et al. US Pub. Pat. Appn. No. 20120318260 disclose nebulizers driven by piezo-electric and/or magnetic drives to generate an aerosol mist.

Other examples include The Technology Partnership PLC, EP615470B1; Hailes et al., U.S. Pat. No. 7,550,897, and Brown et al. U.S. Pat. No. 7,976,135, which disclose liquid projection apparatus employing transducers to project liquid droplets from an outer face of a nozzle.

Finally, Terada et al. U.S. Pat. No. 6,863,224, Yamamoto et al. U.S. Pat. No. 6,901,926, and Esaki et al. U.S. Pat. No. 8,286,629 disclose ultrasonic liquid atomizing devices.

Unfortunately, these expensive components can be contaminated through repeated uses and require careful cleaning or disposal.

What is needed is a relatively low cost system for delivering controlled doses and particle/droplet size aerosol mists.

SUMMARY OF THE INVENTION

Surprisingly, we have found that ultrasonically atomizing a liquid through submillimeter-sized nozzles attached to the end of an elongate sonic horn provides inexpensive aseptic atomization by preventing the liquid contained in the reservoir from touching the ultrasonic horn.

In one embodiment, a handheld misting device has a housing having a dispensing window is arranged and configured to contain a sonic generator, a power source coupled to the sonic generator, at least one reservoir containing a liquid, and a conduit extending from the at least one reservoir to a nozzle removably coupled to the sonic generator. The sonic generator includes a converter and an elongate horn having a proximal end coupled to the converter and a distal end, and the nozzle is removably coupled to the distal end of the horn. Thus, the device delivers the liquid through a delivery opening formed in the nozzle, and activating the sonic generator energizes the liquid in the nozzle to generate an aerosol plume that is delivered through the dispensing window.

BRIEF DESCRIPTION OF THE DRAWING

FIG. 3 is a side view of the disposable cartridge of the handheld aseptic misting device of FIGS. 1 and 2 with the housing removed to show the interior components.

FIGS. 4A-C are perspective views of various nozzle and receptacle combinations useful in the handheld aseptic misting device of FIG. 1.

DETAILED DESCRIPTION OF THE PREFERRED EMBODIMENTS

Figure 1:
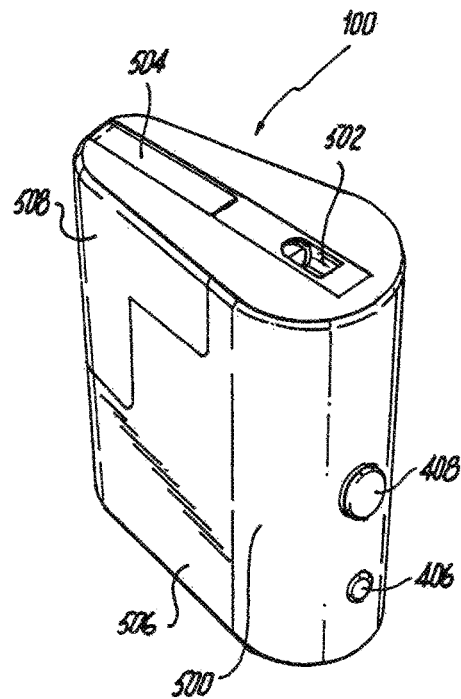
FIG. 1 is a perspective view of a handheld aseptic misting device according to one embodiment of the invention.
Figure 2:
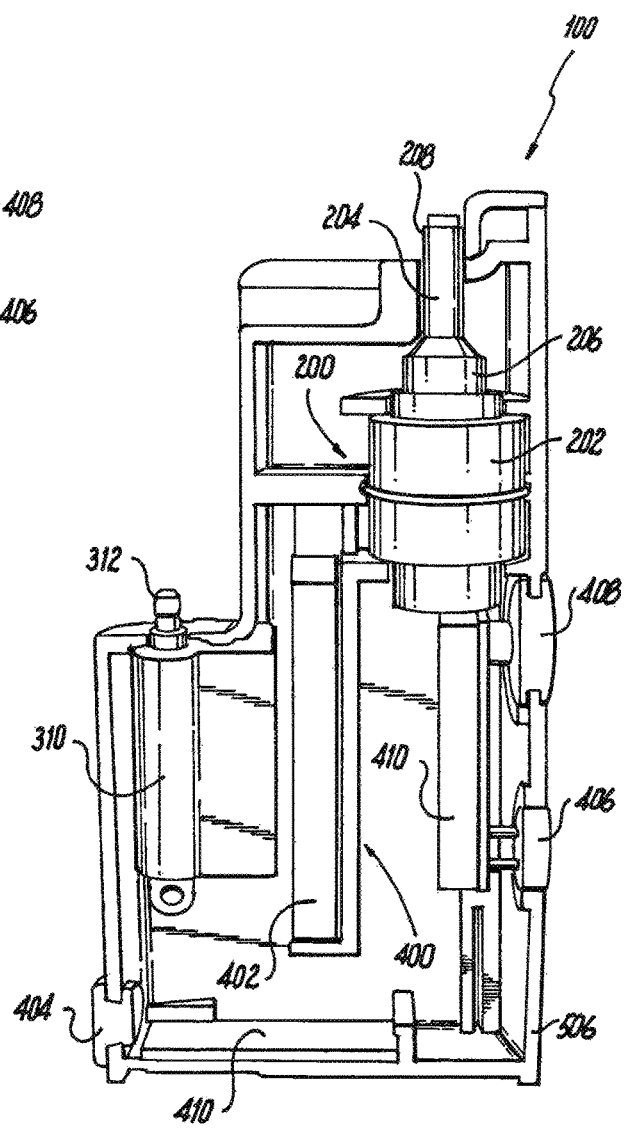
FIG. 2 is a side view of the handheld aseptic misting device of FIG. 1 with the housing removed to show the interior components.

The present invention relates to a handheld sonic misting device that is more economical than conventional sonic misting devices, because the relatively expensive sonic generator and horn are isolated from liquids dispensed by the misting device. Thus, the misting device can be replenished with liquids without significant build-up of liquids on the horn.

In one form of the device, a conduit delivers the liquid to be dispensed to the tip of the horn in a system arranged and configured to direct the liquid away from the horn, such that the horn is not contaminated by the liquid and further, subsequent liquids dispensed from the device are not contaminated by previously dispensed liquids.

As shown in FIGS. 1-5, the handheld misting device 100 (including a sonic generator 200, a liquid delivery system 300, and an electric power and control system 400) useful to form an aerosol comprising liquid droplets (referred to herein as a "mist" or "plume") is contained within a housing 500. The sonic generator 200 includes a converter 202 and an elongate horn 204 having a proximal end 206 coupled to the converter 202 and a distal end 208, opposite thereof, visible through an open dispensing window 502 in the housing 500. The converter 202 is coupled to the electric power and control system 400 through electrical connections, such as wires (not shown).

The liquid delivery system 300 includes a collapsible reservoir 302, a conduit 304, a nozzle 306 having at least one delivery opening 308, and a linear motor 310. The piston 312 of the linear motor 310 contacts the lower surface 314 of the reservoir 302 to force liquid out of reservoir and into conduit 304. The linear motor 310 is also coupled to the electric power and control system 400 through appropriate electrical connections, such as wires (not shown). The conduit 304 conducts liquid from the collapsible reservoir 302 to the nozzle 306, and the nozzle 306 is physically coupled to the distal end 208 of the elongate horn 204. The nozzle 306 is arranged and configured to dispense liquid from the collapsible reservoir 302 to the atmosphere through the dispensing window 502 in the housing 500. The nozzle 306 is protected during storage by closing the dispensing window 502 with a cover 504.

Although the liquid delivery system 300 described above includes a collapsible reservoir 302 and a linear motor 310, one of ordinary skill in the art will recognize that other systems may be used. The collapsible reservoir and linear motor provide one solution to the problem of delivering controlled volumes of liquid from the reservoir. Alternative systems may also be used. For example, the same functionality as the reservoir and pump may be delivered via one or more of the following: pipette, syringe, squeezable bag, pressure actuated reservoir, and even gravity feed.

In order to reduce the cost of operation of the handheld misting device 100 of FIGS. 1-5, the housing 500 includes a first, electromechanical section 506 (shown in FIG. 2) that houses components including the sonic generator 200, the electric power and control system 400, and the linear motor 310 of the liquid delivery system 300, and a second, liquid section 508 (shown in FIG. 3) that houses the collapsible reservoir 302, conduit 304, and nozzle 306 having at least one delivery opening (shown as 308a, 308b, 308c in FIGS. 4A-4C). As shown in FIG. 3, the liquid section 508 is a separate, removable section that can be securely attached to the electromechanical section 506. Alternatively, the liquid section 508 may be an openable compartment in the housing 500 that is arranged and configured to receive replacement collapsible reservoir 302, conduit 304, and nozzle 306.

The electric power and control system 400 includes a power source, such as a rechargeable battery 402, that is electrically connected to an electrical charging port 404 disposed in the housing 500. The electric power and control system 400 also includes an on/off switch 406 and an activation switch 408, both disposed on the housing 500, and one or more control boards 410. The power source is preferably replaceable and/or rechargeable and may include devices such as a capacitor or, more preferably, a battery. In a presently preferred embodiment, the power source 402 is a rechargeable battery including, without limitation, lithium-based cells, including lithium polymer batteries. One example of an internal power source is a lithium polymer cell providing a voltage of about 3.7 V that has a capacity of at least about 200 milliamp hours (mAh).

The interaction between the nozzle (shown as 306a, 306b, 306c in FIGS. 4A-4C) and the distal end 208 of the elongate horn 204 is shown greater detail in FIGS. 4A-4C. The nozzle 306 is securely fitted into a receptacle 210 formed in the distal end 208 of the elongate horn 204. This substantial physical coupling permits the nozzle 306 to vibrate with the distal end 208 of the elongate horn 204 to trigger standing waves that are the provide the ultrasonically driven mist dispensed from the nozzle 306. In preferred embodiments shown in FIGS. 4A-4C, the nozzle 306 extends away from the distal end 208 of the elongate horn 204 to reduce the likelihood of the liquid leaking onto and contaminating the distal end.

In FIG. 4A, the nozzle 306a is substantially cylindrical, comprises a plurality of delivery openings 308a, and fits into a receptacle 210a at the distal end 208a of the elongate horn 204.

In FIG. 4B, the nozzle 306b has a frusto-conical shape, comprises a single, elongate delivery opening 308b, and fits into a receptacle 210b at the distal end 208b of the elongate horn 204.

In FIG. 4C, the nozzle 306c has a trapezoidal cross-section, comprises a substantially rectangular delivery opening 308c, and fits into a receptacle 210c at the distal end 208c of the elongate horn 204.

The size, shape, number, and arrangement of delivery opening(s) 308 in the nozzle 306 define the plume of mist generated by the misting device 100. The delivery opening(s) 308 are dimensioned to delivery an aerosol mist. Preferably, each delivery opening has a maximum dimension (across the opening) of less than about 200 microns (μm), more preferably, between about 50 and about 150 μm. Preferred delivery openings are generally circular, but one of ordinary skill in the art may modify this to achieve specifically desired aerosol properties. The number of delivery openings is selected to deliver a desired misting flow. Nozzles with one delivery opening have been shown to produce a useful aerosol plume, and other nozzles with 6 and 7 openings have also produced useful aerosol plumes. Therefore, one of ordinary skill in the art may select from one to more than ten delivery openings.

Figure 5:
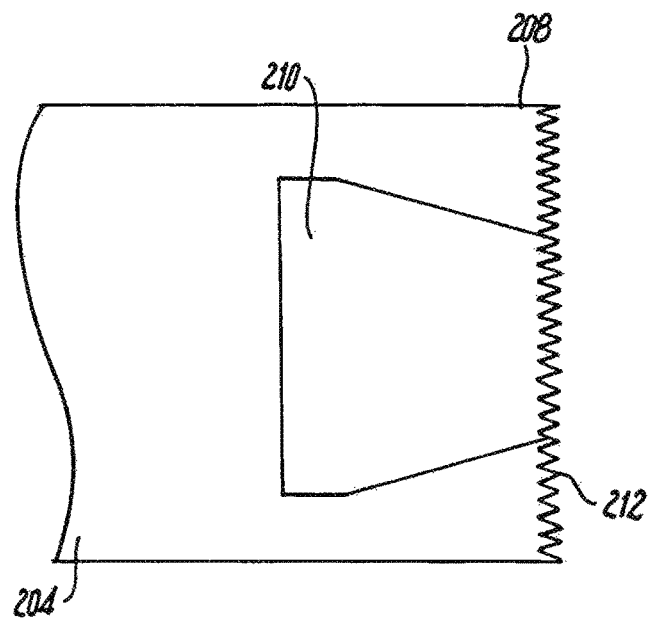
FIG. 5 is a detailed side view of the distal end of the sonic horn having surface features to prevent undesired misting of liquids that may migrate to the distal end of the horn.

The distal end 208 of the elongate horn 204 may have surface features 212 disposed thereon to substantially prevent the formation of a mist from any liquid that may migrate away from the nozzle 306 and to the distal end 208 of the elongate horn 204. As shown in FIG. 5, these surface features 212 have an acute angle with respect to the axis of the horn to prevent any sonic motions from driving undesired liquids into the plume of liquids dispensed from the nozzle 306.

Figure 6:
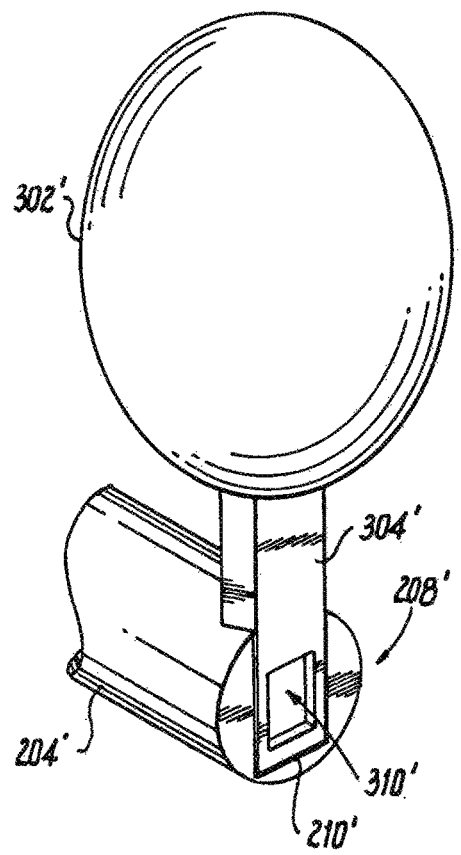
FIG. 6 is a perspective view of elements of a handheld aseptic misting device according to a second embodiment of the invention

In an alternative embodiment shown schematically in FIG. 6, a reservoir 302' feeds a nozzle 306' having an opening 310', e.g., via gravity, through a conduit 304'. Similar to the embodiment of FIGS. 1-5, the nozzle 306' fits into a receptacle 210' formed in the distal end 208' of an elongate horn 204' of a sonic generator (not shown). Activating the sonic generator energizes the liquid in the nozzle 306' to drive it through the delivery opening 310' to generate an aerosol plume. In this embodiment, it is preferred that the height of the liquid column does not introduce significant flow variation during use and/or across multiple uses.

Figure 7:
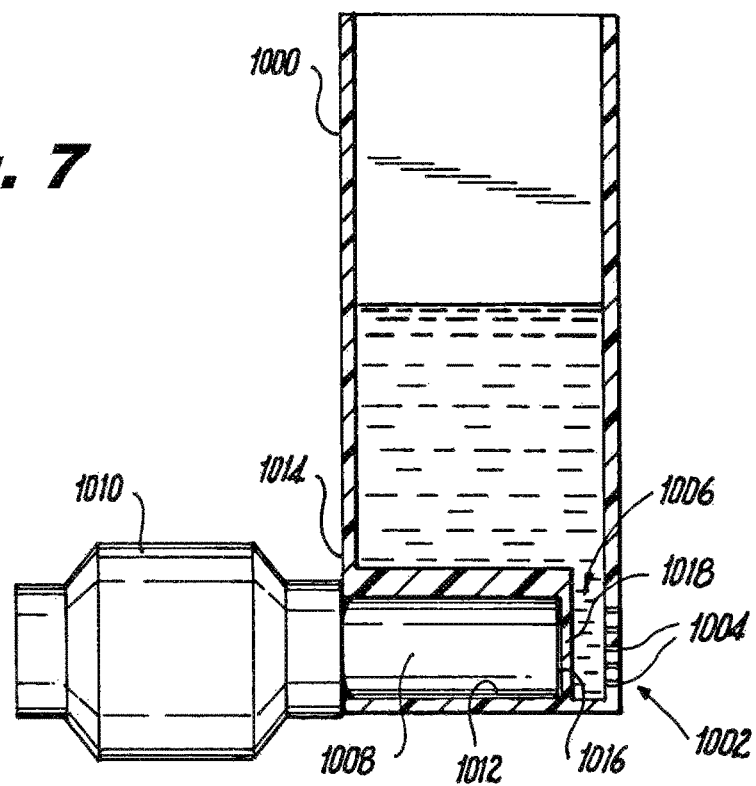
FIG. 7 is a schematic cross-section of a handheld aseptic misting device according to a third embodiment of the invention.

In an alternative embodiment shown schematically in FIG. 7, a reservoir 1000 feeds a nozzle 1002 having a plurality of delivery openings 1004, e.g., via gravity, through conduit 1006. Elongate horn 1008 of sonic generator 1010 fits into receptacle 1012 proximate the base 1014 of reservoir 1000 to enable distal end 1016 of elongate horn 1008 to contact a rear wall 1018 of the nozzle 1002 (opposite the delivery openings 1004). Activating the sonic generator 1010 energizes the liquid in the nozzle 1002 to drive it through the delivery openings 1004 to generate an aerosol plume.

Figure 8:
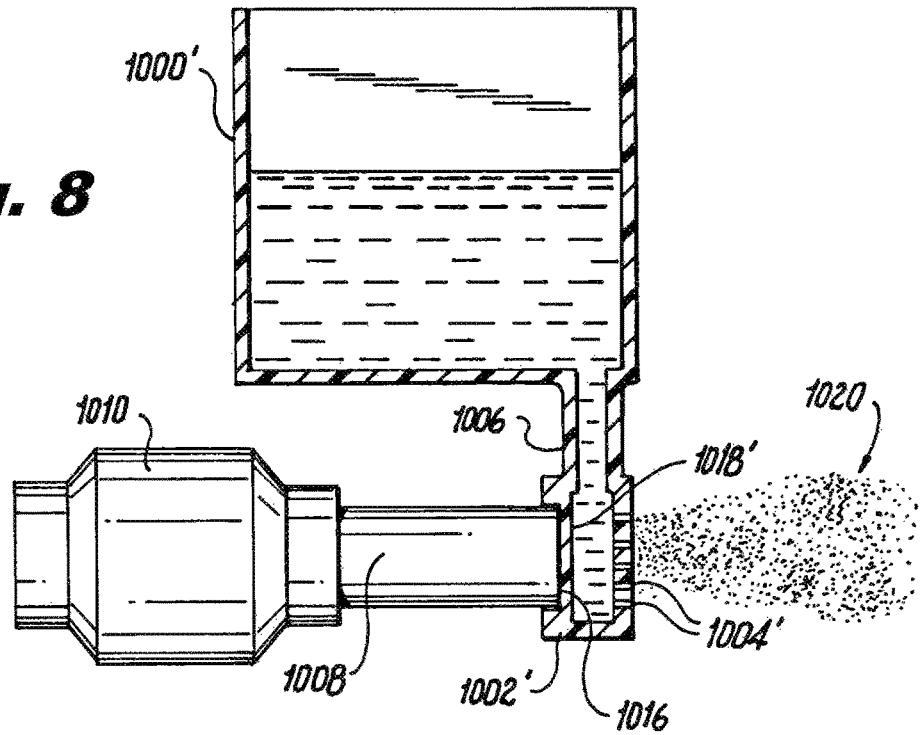
FIG. 8 is a schematic cross-section of a handheld aseptic misting device according to a fourth embodiment of the invention.

In another alternative embodiment shown schematically in FIG. 8, a reservoir 1000' feeds a nozzle in the form of a cap 1002' (dimensioned to engage the distal end of the elongate horn 1008 of the sonic generator 1010) via gravity, through conduit 1006'. Again, the enable distal end 1016 of elongate horn 1008 contacts a rear wall 1018' of the cap 1002'. Activating the sonic generator 1010 energizes the liquid in the nozzle 1002' to drive it through the delivery openings 1004' to generate an aerosol plume 1020.

One of ordinary skill in the art will recognize the general assembly of the handheld sonic misting device of the present invention. However, the interaction of the following elements is important to consider. First the distal end of the horn and the nozzle should fit tightly to minimize energy loss due to inefficient motion transfer from the horn to the wall of the nozzle opposite the delivery openings to minimize heat buildup and to maximize control of the resulting aerosol plume. As the elongate horn is generally metallic, preferably aluminum and/or titanium, the nozzle should be made out of rigid plastic. For example in the embodiment of FIGS. 1-5, the nozzle can be formed of metal or engineering plastic and machined or molded within appropriate tolerances to fit into the receptacle at the distal end of the elongate horn. A non-limiting list of useful materials include acetal resins (such as available from DuPont® Engineering Polymers under the DELRIN® brand), polyether ether ketones, amorphous thermoplastic polyetherimide (PEI) resins (such as available from SABIC under the ULTEM® brand). In addition, in the embodiments of FIGS. 6-8, the nozzle may be formed integrally with the reservoir and of the same materials. Alternatively, the nozzle may be formed from one of the foregoing materials and combined with a reservoir and/or conduit that are formed of less expensive and/or more easily handled materials.

The housing may be fabricated by plastic injection molding, or any other suitable technique, and it is preferably ergonomic and adapted to fit comfortably in a hand of a user. In a preferred embodiment, the housing has a maximum linear dimension (length) of up to about 20 cm, more preferably, up to about 15 cm, and most preferably up to about 10 cm. Preferably, the maximum dimension perpendicular to the length is 8 cm, more preferably, 5 cm.

The conduit between the reservoir and nozzle is preferably sufficiently flexible for ease of manufacture. It is, however, preferred that the diameter of the conduit does not change with the application of pressure to the reservoir to dispense liquid therefrom. This permits control of the volume of liquid dispensed in an application of the aerosol plume.

In a preferred embodiment, the liquid section is removable from the electromechanical section in a manner in which the nozzle is coupleable to the distal end of the elongate horn. For example, the liquid section (e.g., of FIG. 3, or any of FIGS. 6-8) may be slidably engageable with the electromechanical section with the nozzle of FIGS. 4A-4C or the like oriented to slide into the receptacle of the horn. Alternately, the cap 1002', of the embodiment of FIG. 8 may snap fit over the distal end of the horn.

The present invention is useful in the delivery of aerosol plumes of medication and/or moisturizing solutions in a more sanitary manner than currently provided. Sonic generation of aerosol plumes can provide very fine mists, having a droplet size between about 20 and about 60 μm, given by the practical range of frequencies for the ultrasonic horn between 20 kHz and 200 kHz. As indicated above, as sonic generators are more expensive than traditional squeeze and spray bottles, it is important to separate the expensive and reusable sonic generator and horns from the relatively inexpensive and potentially disposable liquid reservoirs. Therefore, in use, a replaceable liquid section 508, such as shown in FIG. 3, can be slidably inserted into the electromechanical section 506. As a result of this, the distal end 208 of the elongate horn 204 is engaged with the nozzle 306. Any protective covering (e.g., cover 504) can be removed from the nozzle, 306, and the misting device 100 can be energized.

To create an aerosol plume, the activation switch 408 is depressed, and the linear motor 310 drives the piston 312 to deliver a controlled force on the lower surface of the reservoir 314. This action forces liquid through conduit 304 to nozzle 306 and delivery opening(s) 308. This sequence may be repeated until the reservoir is emptied. The now-empty liquid section 508 can be removed and a new liquid section 508, including a new nozzle 306, is inserted. The new nozzle is not contaminated as a result of the previous use of the misting device.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A handheld misting device comprising a housing having a dispensing window, the housing comprising:
   a) an electromechanical section comprising:
      i) a sonic generator comprising a converter and an elongate horn having a proximal end coupled to the converter and a distal end having a receptacle formed therein; and
      ii) a power source coupled to the sonic generator; and
   b) a liquid section arranged and configured to be securely attachable to the electromechanical section and to contain:
      i) at least one reservoir containing a liquid; and
      ii) a conduit extending from the at least one reservoir to a nozzle removably inserted into the receptacle formed in the distal end of the horn to deliver the liquid through a delivery opening formed in the nozzle, whereby activating the sonic generator energizes the liquid in the nozzle to generate an aerosol plume that is delivered through the dispensing window.

2. The handheld misting device of claim 1 wherein the liquid section is disposable.

3. The handheld misting device of claim 1 wherein the at least one reservoir containing the liquid comprises a collapsible reservoir coupled to a linear motor to control delivery of the liquid through the conduit to the nozzle.

4. The handheld misting device of claim 1 wherein the nozzle is arranged and configured for removable placement over the distal end of the elongate horn.

5. The handheld misting device of claim 1 wherein the liquid section is arranged and configured for slidable engagement with the electromechanical section.

* * * * *